United States Patent [19]

Ando

[11] Patent Number: 5,059,025
[45] Date of Patent: Oct. 22, 1991

[54] SPECTROPHOTOMETER

[75] Inventor: Osamu Ando, Kyoto, Japan

[73] Assignee: Shimadzu Corporation, Kyoto, Japan

[21] Appl. No.: 500,972

[22] Filed: Mar. 29, 1990

[30] Foreign Application Priority Data

Mar. 31, 1989 [JP] Japan ................................. 1-82461

[51] Int. Cl.$^5$ ........................ G01J 3/02; G01N 21/13
[52] U.S. Cl. .................................. 356/319; 356/244; 356/440
[58] Field of Search ............... 356/319, 323, 325, 326, 356/328, 244, 246, 440

[56] References Cited

U.S. PATENT DOCUMENTS 3,544,225 12/1970 Wattenburg et al. ............... 356/440

Primary Examiner—F. L. Evans
Attorney, Agent, or Firm—Armstrong, Nikaido, Marmelstein, Kubovcik & Murray

[57] ABSTRACT

A spectrophotometer having a movable sample cell holder, formed with position detecting through-holes, for holding sample cells and a detector for measuring the light transmitting the through-hole to detect a position of the holder.

2 Claims, 2 Drawing Sheets

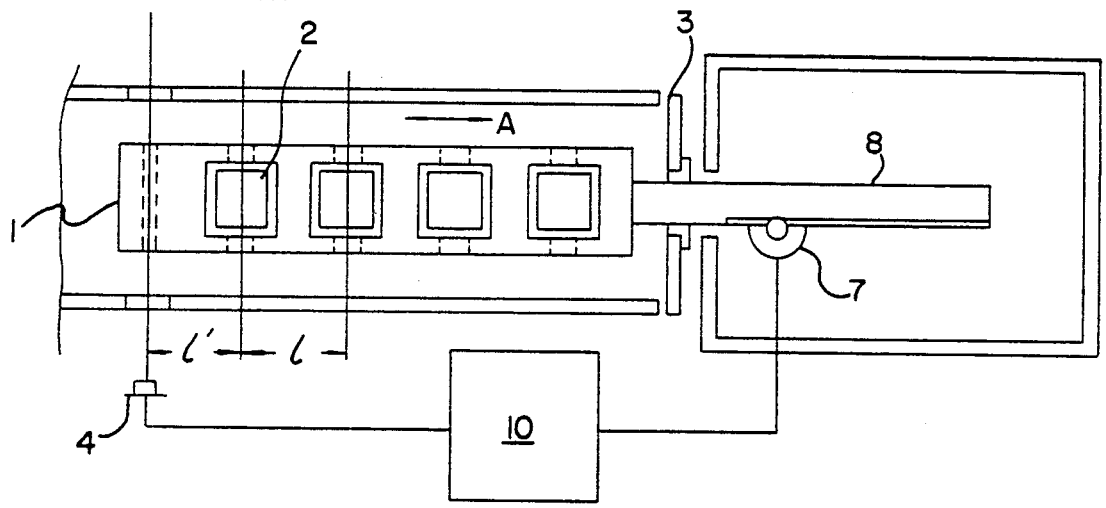
FIG. 1(A)
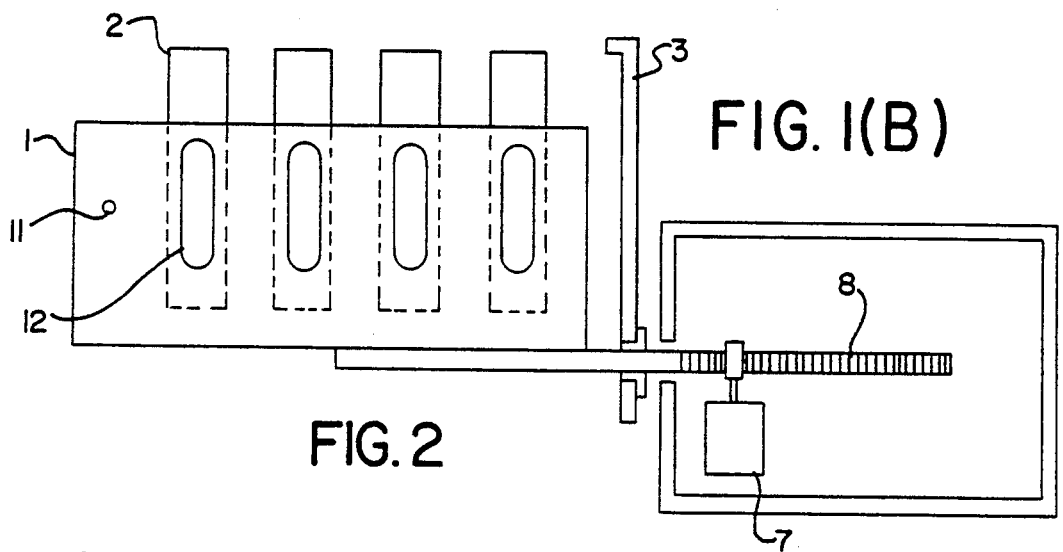
FIG. 1(B)
FIG. 2
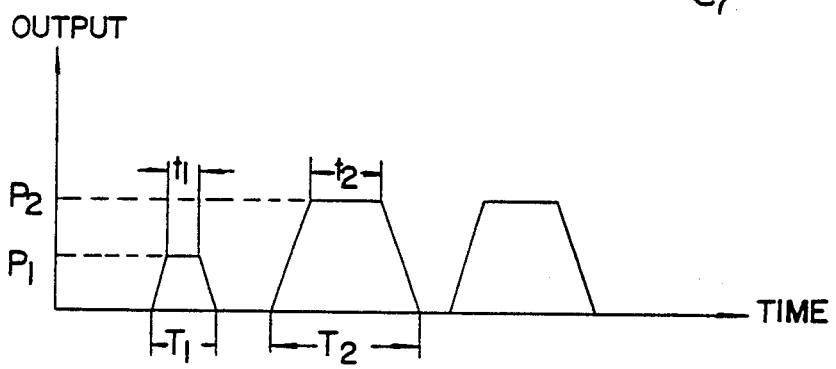

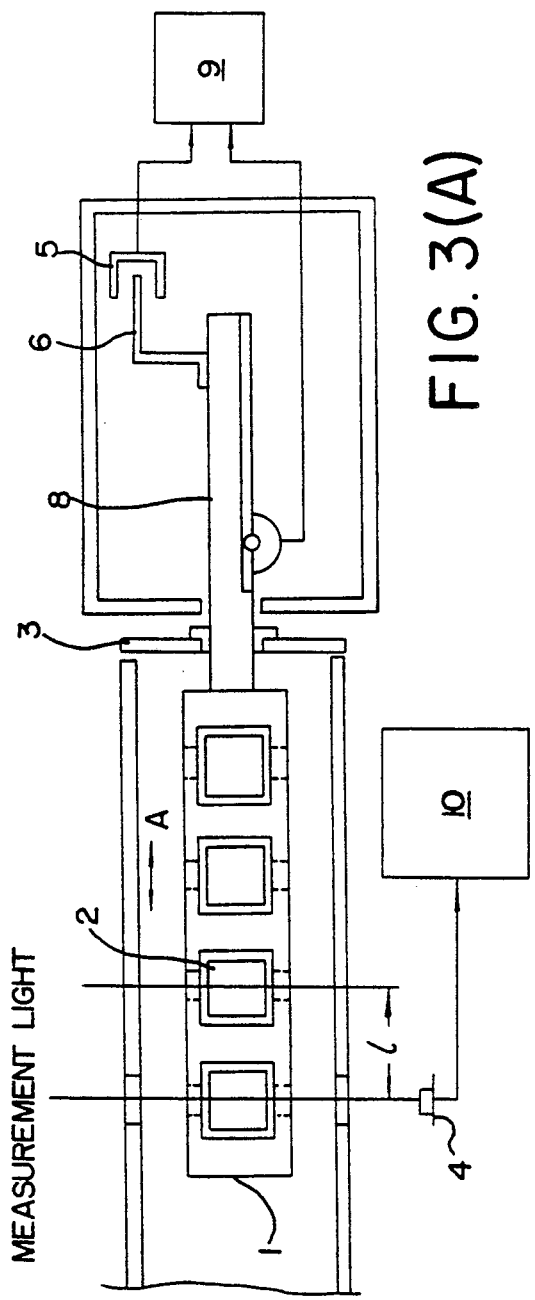
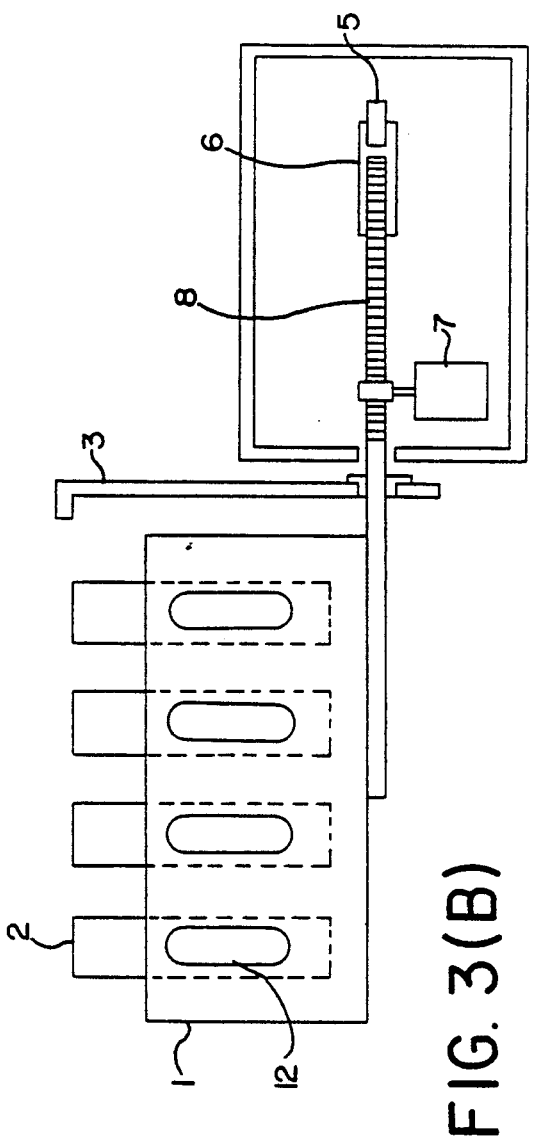
FIG. 3(A)
FIG. 3(B)

SPECTROPHOTOMETER

BACKGROUND OF THE INVENTION

The present invention is directed generally to a spectrophotometer, and more particularly, to a cell positioner for controlling the position of a movable sample holder for holding a plurality of sample cells in a sample chamber.

A typical arrangement of a prior art cell positioner is that, as depicted in FIG. 3, a position detector composed of a photointerrupter 5 and a position detecting plate 6 is mounted on a driving system (a unit for transferring power given from a driving motor 7) of the sample cell holder 1, whereby positions of sample cells 2 are detected and controlled under control of an open loop in which an interval L between the sample cells is a known factor with a point, serving as an origin, at which the position detecting plate 6 shields a flux of light of the photointerrupter 5.

The prior art cell positioner, however, presents the following problems. It is required that a position to mount the position detector (including the photointerrupter and the position detecting plate) be accurately adjusted in a moving direction of the sample cell holder in order to direct measurement light of a spectrophotometer spot-on to the center of the sample cell. This adjustment has to be carried out while confirming a stop position of the sample cell holder and a light measuring position, which requires a readjustment for every unit depending on a scatter within an adjusted error range in the optical system of the spectrophotometer as well as being troublesome.

SUMMARY OF THE INVENTION

It is a primary object of the present invention, which has been devised to obviate the forgoing problems inherent in the prior arts, to provide a cell positioner capable of invariably positioning a sample cell (holder) exactly in a position of light flux to be measured even if there is a scatter in the light flux measuring position in the spectrophotometer by eliminating a necessity for a position detector and therefore making no positional adjustment of the detector.

To accomplish the foregoing object, according to one aspect of the invention, there is provided a spectrophotometer comprising: a shielded sample chamber; a plurality of sample cells; a movable sample holder, formed in its side surfaces with position detecting through-holes, for holding the sample cells; and a detector for measuring rays of measurement light which have transmitted the through-holes, thus detecting and controlling the position of the sample cell holder.

Based on this construction, though a single through-hole may suffice, for higher precision, preferably a plurality of position detecting through-holes having diameters different from each other, but well smaller than that of each measuring through-hole, are perforated in the sample cell holder in a moving direction thereof corresponding to the measuring through-holes with a sufficiently relative positional accuracy with respect to the measuring through-holes, thereby allowing the detection of the moving direction of the sample cell holder.

The sample cell holder is shaped by die-cast molding, injection molding and machining, whereby the position detecting through-holes can be accurately formed.

Th sample cell holder is moved by driving the thus constructed cell positioner, and the measuring detector functions to detect the rays of measurement light which have transmitted through the position through-holes, wherein that position serves as an original position of the sample cell holder.

An interval between the original position and the closest sample cell and an interval between the sample cells are previously known, and it is therefore easy to effect positioning by aligning the sample cell with the center of measurement light while moving the sample cell holder.

BRIEF DESCRIPTION OF THE DRAWINGS

Other objects and advantages of the present invention will become apparent during the following discussion taken in conjunction with the accompanying drawings, in which:

FIG. 1(A) is a plan view depicting a cell positioner according to the present invention;

FIG. 1(B) is a side view illustrating the cell positioner thereof;

FIG. 2 is a diagram a light measuring output of a detector;

FIG. 3(A) is a plan view depicting a prior art cell positioner; and

FIG. 3(B) is a side view of the same cell positioner.

DESCRIPTION OF THE PREFERRED EMBODIMENT

An illustrative embodiment of the present invention will hereinafter be described with reference to the accompanying drawings.

Turning first to FIG. 1, a cell positioner consists of a sample cell holder 1 for holding four pieces of angular sample cells 2 in a shielded sample chamber and a driving motor 7, fixed to a bottom of the sample cell holder 1, for driving the sample cell holder 1 in an arrowed direction A through a power transferring unit 8 protruding from the sample chamber 3. Position detecting through-holes 11 are perforated in side surfaces of the sample cell holder 1 in addition to measuring through-holes 12 formed corresponding to the sample cells 2.

A diameter of the position detecting through-hole 11 is set sufficiently smaller than that of the measuring through-hole 12. With this arrangement, a measuring detector 4 receives and measures rays of measurement light of a spectrophotometer which have passed through the measuring through-holes 12 as well as through the position detecting through-holes 11 while moving the sample cell holder 1 in the arrowed direction A. As illustrated in FIG. 2, there are obtained a light measuring output value P1 with time widths T1 and t1 in connection with the position detecting through-hole 11 and a light measuring output value P2 with time widths T2 and t2 in connection with the measuring through-hole 12. Two types of the rough-holes 11 and 12 can readily be identified by making comparisons with respect to the time widths and/or the output values.

The original position of the sample cell holder 1 is set in a position where the position detecting through-hole 11 is detected, and more precisely a mid-point of the light measuring output time width t1 from the through-hole 11 is obtained.

When the sample cell holder 1 is shaped by, e.g., die-cast molding, the position detecting through-holes 11 can be perforated with a sufficient relative positional accuracy with respect to the measuring through-holes 12 (intervals L').

Note that the comparison of the light measuring outputs from the measuring detector 4 for detecting the original position of the sample cell holder 1, calculation of the original position and driving of the sample cell holder 1 involve the use of a highly sophisticated A/D converter, typically built in a control unit 10 of the spectrophotometer, for measuring the light and a data processing function incorporated therein.

As discussed above, in accordance with the present invention having the foregoing construction, it is possible to accurately position the sample cell holder in the light measuring position, even if there is caused a scatter in the position of a light flux of the spectrophotometer. For this purpose, as a matter of course, no special position detector is needed, and hence the necessity for an adjustment of the position detector may be eliminated.

Although the illustrative embodiment of the present invention has been described with reference to the accompanying drawings, it is to be understood that the present invention is not limited to that precise embodiment. A variety of modifications or changes may be effected by one skilled in the art without departing from the scope or spirit of the invention.

What is claimed is:

1. A spectrophotometer, comprising:
   a shielded sample chamber;
   a plurality of sample cells;
   a movable sample holder for supporting said plurality of sample cells, wherein said holder has a plurality of sampling through-holes, corresponding to said sample cells and spaced apart from one another in the direction of movement at a predetermined interval, to allow light to flow into and out of said sample cells, and at least one position detecting through-holes, having a diameter significantly less than said sampling through-holes, wherein said position detecting through-hole is spaced from one of said sampling through-holes at said predetermined interval;
   a light source means for projecting light through said sampling and position detecting through-holes;
   a detecting means for detecting light projected through said sampling through-holes and said detecting through-holes; and
   a control means, receiving an output of said detecting means, for controlling movement of said holder in response to said detecting means.

2. The spectrophotometer of claim 1, wherein said movable sample holder has a plurality of position detecting through-holes having diameter different from one another, but significantly less than said sample through-holes.

* * * * *